(12) United States Patent
Jafari

(10) Patent No.: US 6,602,208 B2
(45) Date of Patent: *Aug. 5, 2003

(54) GUIDEWIRE WITH TUBULAR CONNECTOR

(75) Inventor: Mo Jafari, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/862,670

(22) Filed: May 21, 2001

(65) Prior Publication Data

US 2002/0032390 A1 Mar. 14, 2002

Related U.S. Application Data

(63) Continuation of application No. 09/382,431, filed on Aug. 24, 1999, now Pat. No. 6,248,082, which is a continuation of application No. 08/948,770, filed on Oct. 10, 1997, now Pat. No. 5,980,471.

(51) Int. Cl.[7] .................................................. A61B 5/00
(52) U.S. Cl. ....................................... 600/585; 600/434
(58) Field of Search ............................... 600/433, 434, 600/435, 585

(56) References Cited

U.S. PATENT DOCUMENTS

| | | | |
|---|---|---|---|
| 4,665,906 A | 5/1987 | Jervis | 606/78 |
| 4,827,941 A | 5/1989 | Taylor et al. | 600/434 |
| 4,846,193 A | 7/1989 | Tremulis et al. | 600/585 |
| 4,925,445 A | 5/1990 | Sakamoto et al. | 604/528 |
| 5,109,867 A | 5/1992 | Twyford, Jr. | 600/585 |
| 5,188,621 A * | 2/1993 | Samson | 604/528 |
| 5,195,535 A | 3/1993 | Shank | 600/585 |
| 5,234,002 A | 8/1993 | Chan | 600/585 |
| 5,247,942 A | 9/1993 | Prather et al. | 600/585 |
| RE34,466 E | 12/1993 | Taylor et al. | 600/434 |
| 5,267,573 A | 12/1993 | Evans et al. | 600/585 |
| 5,271,415 A | 12/1993 | Foerster et al. | 600/585 |
| 5,282,478 A | 2/1994 | Fleischhaker, Jr. et al. | 600/585 |
| 5,341,818 A | 8/1994 | Abrams et al. | 600/585 |
| 5,365,943 A | 11/1994 | Jansen | 600/585 |
| 5,365,944 A | 11/1994 | Gambale | 600/585 |
| 5,404,886 A | 4/1995 | Vance | 600/585 |
| 5,415,178 A * | 5/1995 | Hsi et al. | 600/585 |
| 5,421,348 A | 6/1995 | Larnard | 600/585 |
| 5,511,559 A | 4/1996 | Vance | 600/585 |
| 5,980,471 A * | 11/1999 | Jafari | 600/585 |
| 6,001,068 A * | 12/1999 | Uchino et al. | 600/585 |
| 6,248,082 B1 * | 6/2001 | Jafari | 600/585 |

FOREIGN PATENT DOCUMENTS

| | | |
|---|---|---|
| EP | 0 313 807 A1 | 5/1989 |
| EP | 0 838 230 A2 | 4/1998 |
| EP | 0 838 230 A3 | 6/1998 |
| WO | WO 95/08294 | 3/1995 |

* cited by examiner

*Primary Examiner*—Charles A Marmor, II
(74) *Attorney, Agent, or Firm*—Fulwider Patton Lee & Utecht, LLP

(57) ABSTRACT

An improved guidewire for advancing a catheter within a body lumen which has a high strength proximal core section, a flexible distal core section preferably formed of pseudoelastic alloy and a connecting element to provide a torque transmitting coupling between the distal end of the proximal core section and the proximal end of the distal core section. The ends of the core sections are secured within the inner lumen of the connecting element by means of a hardened mass of bonding material. The wall of the connecting element is provided with an opening to facilitate the introduction of the hardenable bonding material in the pourable state into the inner lumen of the connecting element. Preferably at least one of the ends of the core sections are configured, e.g. enlarged in at least one dimension compared to an adjacent part of the core section, to develop a mechanical interlock within the mass of hardened material.

14 Claims, 2 Drawing Sheets

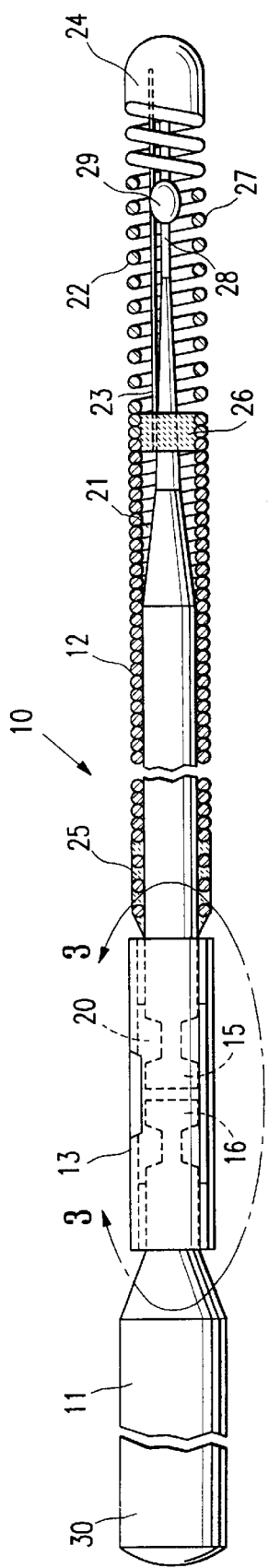
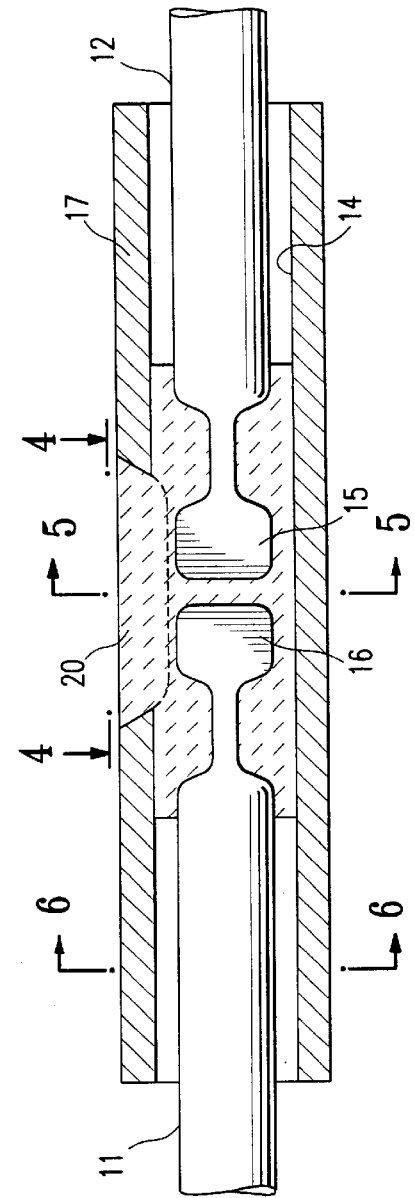
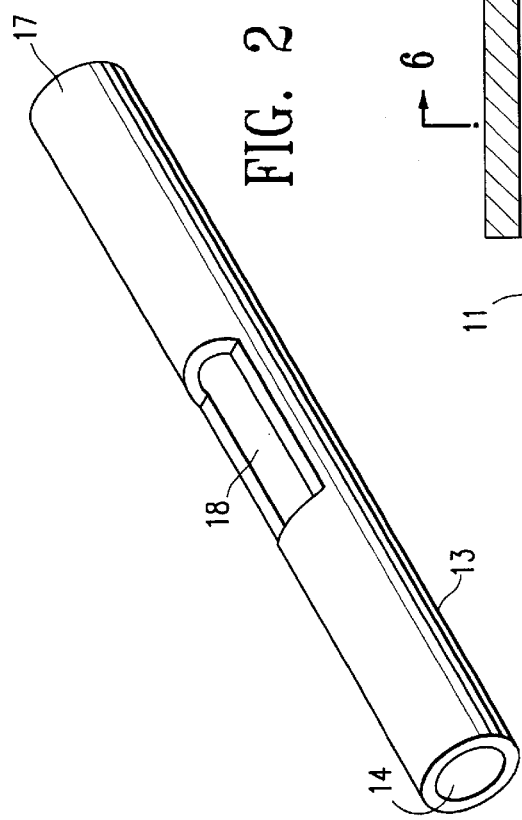

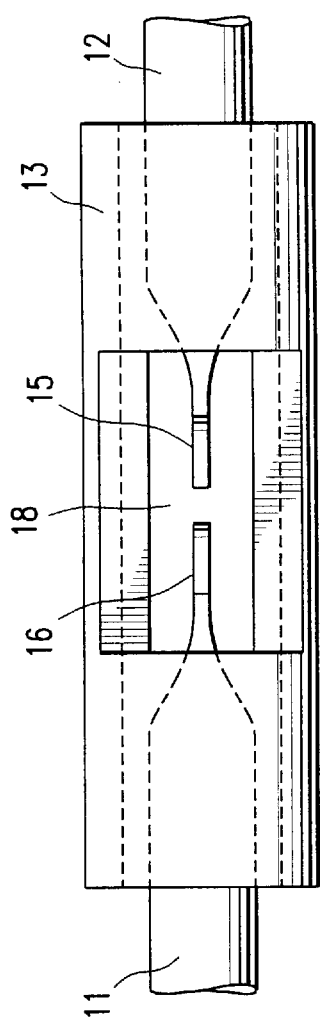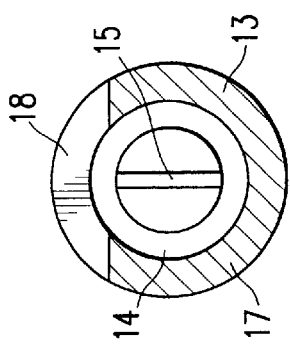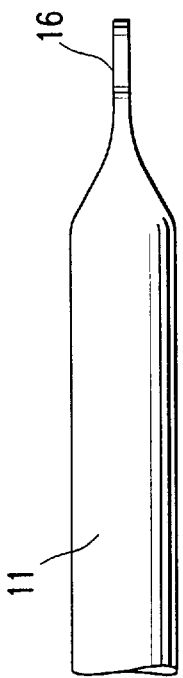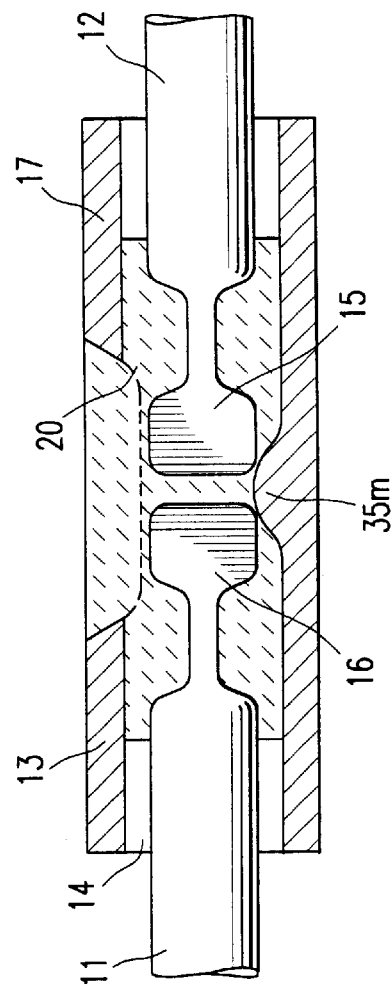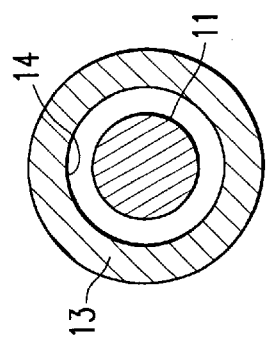

GUIDEWIRE WITH TUBULAR CONNECTOR

This application is a continuation of U.S. patent application Ser. No. 09/382,431, of Mo Jafari, entitled "GUIDEWIRE WITH TUBULAR CONNECTOR," filed on Aug. 24, 1999, now U.S Pat. No. 6,248,082; which in turn is a continuation of U.S. patent application Ser. No. 08/948,770, of Mo Jafari, entitled "GUIDEWIRE WITH TUBULAR CONNECTOR," filed on Oct. 10, 1997, now U.S. Pat. No. 5,980,471; both of which are hereby incorporated herein by reference in their entirety.

BACKGROUND OF THE INVENTION

This invention relates to the field of medical devices, and more particularly to a guidewire for advancing a catheter within a body lumen in a procedure such as percutaneous transluminal coronary angioplasty (PTCA).

Conventional guidewires for angioplasty and other vascular procedures usually comprise an elongated core member with one or more tapered sections near the distal end thereof and a flexible body such as a helical coil disposed about the distal portion of the core member. A shapable member, which may be the distal extremity of the core member or a separate shaping ribbon which is secured to the distal extremity of the core member extends through the flexible body and is secured to a rounded plug at the distal end of the flexible body. Torquing means are provided on the proximal end of the core member to rotate, and thereby steer, the guidewire while it is being advanced through a patient's vascular system.

In a typical PTCA procedure a guiding catheter having a preformed distal tip is percutaneously introduced into the cardiovascular system of a patient in a conventional Seldinger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon is inflated to a predetermined size with radiopaque liquid at relatively high pressures (e.g. greater than 4 atmospheres) to compress the arteriosclerotic plaque of the lesion against the inside of the artery wall and to otherwise expand the inner lumen of the artery. The balloon is then deflated so that blood flow is resumed through the dilated artery and the dilatation catheter can be removed therefrom.

A major requirement for guidewires is that they have sufficient column strength to be pushed through a patient's vascular system or other body lumen without kinking. However, they must also be flexible enough to avoid damaging the blood vessel or other body lumen through which they are advanced. Efforts have been made to improve both the strength and flexibility of guidewires to make them more suitable for their intended uses, but these two properties are for the most part diametrically opposed to one another in that an increase in one usually involves a decrease in the other.

The prior art makes reference to the use of alloys such as NITINOL (Ni—Ti alloy) which have shape memory and/or superelastic or pseudoelastic characteristics in medical devices which are designed to be inserted into a patient's body. The shape memory characteristics allow the devices to be deformed to facilitate their insertion into a body lumen or cavity and then be heated within the body so that the device returns to its original shape. Pseudoelastic characteristics on the other hand generally allow the metal to be deformed and restrained in the deformed condition to facilitate the insertion of the medical device containing the metal into a patient's body, with such deformation causing a stress induced phase transformation from austenite to martensite. Once within the body lumen, the restraint on the pseudoelastic member can be removed, thereby reducing the stress therein so that the pseudoelastic member can return to its original undeformed shape by the transformation from the thermally unstable martensite phase back to the original stable austenite phase.

Alloys having shape memory/pseudoelastic characteristics generally have at least two phases, the martensite phase, which has a relatively low tensile strength and which is stable at relatively low temperatures, andgan austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable. The shape of the metal during this heat treatment is the shape "remembered". The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape.

The prior methods of using the shape memory characteristics of these alloys in medical devices intended to be placed within a patient's body presented operational difficulties. For example, with shape memory alloys having a stable martensite temperature below body temperature, it was frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices could be introduced into a patient's body with little or no problem, but they had to be heated to the martensite-to-austenite transformation temperature which was frequently high enough to cause tissue damage and very high levels of pain.

When stress is applied to a specimen of a metal such as NITINOL exhibiting pseudoelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first yields elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as pseudoelasticity or pseudoelasticity.

The prior art makes reference to the use of metal alloys having pseudoelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

The Sakamoto et al. patent discloses the use of a nickel-titanium pseudoelastic alloy in an intravascular guidewire which could be processed to develop relatively high yield strength levels. However, at the relatively high yield stress levels which cause the austenite-to-martensite phase transformation characteristic of the material, it did not have a very extensive stress-induced strain range in which the austenite transforms to martensite at relative constant stress. As a result, frequently as the guidewire was being advanced through a patient's tortuous vascular system, it would be stressed beyond the pseudoelastic region, i.e. develop a permanent set or even kink which can result in tissue damage. This permanent deformation would generally require the removal of the guidewire and the replacement thereof with another.

Products of the Jervis patent on the other hand had extensive strain ranges, i.e. 2 to 8% strain, but the relatively constant stress level at which the austenite transformed to martensite was very low, e.g. 50 ksi.

In U.S. Pat. No. 5,341,818 (Abrams et al.), which has been assigned to the present assignee, reference is made to a guidewire having a stainless steel proximal core section, a flexible distal core section formed of superelastic or pseudoelastic nickel-titanium alloy and a cylindrical connecting element engaging the distal end of the proximal core section and the proximal end of the distal core section to provide a torque transmission relationship between the proximal and distal core sections of the guidewire. The guidewire described and claimed in U.S. Pat. No. 5,341,818 is sold under the trademark Balance Guidewire by the present assignee, Advanced Cardiovascular Systems, Inc. and has met with much commercial success. However, notwithstanding the commercial success of this guidewire product, the manufacturing procedures were quite complicated due to the requirement of etching and precoating the distal core section and the cylindrical connecting element, both of which were formed of NiTi alloy, with a solder material to develop a sound subsequent soldered bond within the cylindrical connector as described in the aforesaid Abrams et al. patent.

SUMMARY OF THE INVENTION

The present invention is directed to an improved guidewire having an elongated core member which has an elongated proximal core section and a flexible distal core section, with the distal end of the proximal core section and the proximal end of the distal core section being secured within a cylindrical connecting element in a torque transmitting relationship. The cylindrical connecting element is provided with an opening in the wall thereof to facilitate the introduction of a hardenable material into the interior of the connecting element which when hardens secures both ends of the core section therein.

Preferably, at least one and preferably both of the ends of the core sections disposed within the interior of the cylindrical connecting element are provided with means to facilitate interlocking with the hardenable material when it hardens within the connecting element. In one presently preferred embodiment one or both ends of the core sections disposed within the cylindrical connecting element are enlarged with at least one transverse dimension greater than transverse dimensions of portions of the core sections adjacent thereto in order to provide a mechanical interlock within the connecting element when the mass of hardenable bonding material which is disposed about the ends of the core sections hardens within the interior of the connecting element. If the hardenable material naturally bonds to the material of one of the ends of the core sections, there may be no need to provide an enlarged dimension on that end to develop a mechanical interlock when the bonding material hardens. If one of the core sections is a titanium containing alloy such as NiTi alloy, special surface treatments and coatings are not required as in the procedures.described in U.S. Pat. No. 5,341,818 to develop a bond between a solder material and the titanium containing alloy. Other means may be employed to create a mechanical interlock between the ends of the guidewire sections within the connecting element. For example, one or more passages may be provided through one or more ends of the core sections into which the hardenable material can penetrate and harden.

The connecting member may be formed of suitable material such as stainless steel, nickel-titanium alloy or even high strength polymeric materials such as polyimide, polycarbonates, PEEK and the like, so long as there is an effective torque transmitting relationship between the proximal and distal core sections. If the hardenable bonding material is not bondable to the interior of the cylindrical surface of the connecting member it may be desirable to provide a protrusion or a recess which will develop a mechanical interlock between the hardened bonding material and the connecting element to preclude relative movement therebetween.

Providing an opening within the wall of the connecting element which provides access to the interior of the connecting element greatly simplifies the assembly procedure for the guidewire. The ends of the core sections are inserted into the interior of the connecting element through the ports in the ends of the member. Hardenable material is introduced into the interior of the connecting element through the opening in the wall surrounding both ends of the core sections therein so that upon hardening, the bonding material fixes the core sections into a torque transmitting relationship. The hardenable material can be solder, e.g., solder consisting of essentially 60%–85% by weight gold and the balance essentially tin, an adhesive or other hardenable polymeric materials.

These and other advantages of the invention will become more apparent from the following detailed description thereof when taken in conjunction with the following exemplary drawings.

BRIEF DESCRIPTION OF THE DRAWINGS

FIG. 1 is an elevational view, partially in section, of a guidewire which embodies features of the invention.

FIG. 2 is a schematic perspective view of the connecting element shown in FIG. 1.

FIG. 3 is a longitudinal cross sectional view of the guidewire shown in FIG. 1 taken along the lines 3—3.

FIG. 4 is an elevational view of the guidewire connection shown in FIG. 3 taken along the lines 4—4 above the notch in the connecting element with the hardened mass of bonding material removed to illustrate the positioning of the proximal end of the distal core section and the distal end of the proximal core section.

FIG. 5 is a transverse cross-sectional view of the guidewire connection shown in FIG. 3 taken along the lines 5—5 with the hardened mass of bonding material removed for purposes of clarity.

FIG. 6 is a transverse cross-sectional view of the guidewire connection shown in FIG. 3, taken along the lines 6—6.

FIG. 7 is an elevational view of the distal end of the proximal core section along the plane of the flattened section.

FIG. 8 is a longitudinal cross sectional view, similar to that shown in FIG. 3, of an alternative guidewire connection with the connecting element having a inner protrusion to fix the mass of hardened bonding material within the interior of the connecting element.

DETAILED DESCRIPTION OF THE INVENTION

FIG. 1 illustrates a guidewire 10 embodying features of the invention that is adapted adapted to be inserted into a patient's body lumen, such as an artery or vein. The guidewire 10 comprises an elongated, relatively high strength proximal core section 11, a relatively short flexible distal core section 12 and a tubular connecting element 13. The tubular connecting element 13, which is shown in detail in FIG. 2, is a hollow elongated element having an interior or inner lumeri 14 extending therein which is adapted to receive the proximal end 15 of the distal core section 12 into a first port of the tubular connection element and the distal end 16 of the proximal core section 11 into a second port of the tubular connecting element. The connector element 13 generally has a cylindrical wall 17 which defines the interior 14 and the wall is provided with an opening 18 which allows for the introduction of hardenable bonding material into the interior after the ends of the guidewire core sections are inserted into the interior. As shown more clearly in FIGS. 3–6, the proximal end 15 of the distal core section 12 is enlarged in at least one dimension compared to an adjacent portion of.the distal core section so as to be fixed within the hardened mass of bonding material 20, disposed within the interior 14 of the connector 13. The distal end 16 of the proximal core section 11 is similarly, although optionally, enlarged compared to an adjacent portion of the proximal core section to be likewise fixed within the hardened mass 20 of bonding material. The hardened mass of bonding material 20 can be solder consisting essentially of 60–85% by weight gold and the balance essentially tin, an adhesive or other hardenable polymeric materials. With this connection, the proximal core section 11 is in a torque transmitting relationship with the distal core section 12.

The connection between the proximal and distal core sections is made by first positioning the enlarged proximal end 15 of the distal core section 12 and the enlarged distal end 16 of the proximal core section 11 in close proximity within the inner lumen 14 of the tubular connecting element 13. Hardenable bonding material in a pourable state is introduced into the interior 14 of the connector 13 through the opening 18 to surround both ends of the core sections within the interior. When the bonding material hardens into mass 20 the enlarged ends 15 and 16 are fixed within the connecting element to facilitate torque transmission therebetween. Preferably, enough of the hardenable material is introduced so that, when hardened, the notch which forms the opening 18 is filled so as to provide an entirely smooth exterior surface to the connecting element 13. If desired, the connecting element may be provided with a protrusion 35m, such as shown in FIG. 8 to fix the hardened mass 20 within the interior 14 of the connecting element.

The guidewire 10 shown in FIG. 1 generally has conventional features. The distal core portion 12 has at least one tapered section 21 which becomes smaller in the distal direction. A helical coil 22 is disposed about the distal core section 12 and is secured by its distal end to the distal end of shaping ribbon 23 by a mass of solder which forms rounded plug 24 when it solidifies. The proximal end of the helical coil 22 is secured to the distal core section 12 at a proximal location 25 and at intermediate location 26 by a suitable solder. The proximal end of the shaping ribbon 23 is secured to the distal core portion 12 at the same intermediate location 26 by the solder. Preferably, the most distal section 27 of the helical coil 22 is made of radiopaque metal, such as platinum or platinum-nickel alloys, to facilitate the fluoroscopic observation thereof while it is disposed within a patient's body. The most distal section 27 of the coil 22 should be stretched about 10 to about 30% in length to provide increased flexibility.

The most distal part 28 of the distal core section 12 is flattened into a rectangular cross-section and is preferably provided with a rounded tip 29, e.g. solder, to prevent the passage of the most distal part through the spacing between the stretched distal section 27 of the helical coil 22.

The exposed portion of the elongated proximal core section 11 should be provided with a coating 30 of lubricous material such as polytetrafluoroethylene (sold under the trademark Teflon® by Du Pont, de Nemours & Co.) or other suitable lubricous coatings such as other fluoropolymers, hydrophilic coatings and polysiloxane coatings.

The elongated proximal core section 11 of the guidewire 10 is generally about 130 to about 140 cm in length with an outer diameter of about 0.006 to 0.018 inch (0.15–0.45 mm) for coronary use. Larger diameter guidewires, e.g. up to 0.035 inch (0.89 mm) or more may be employed in peripheral arteries and other body lumens. The lengths of the smaller diameter and tapered sections can range from about 1 to about 20 cm, depending upon the stiffness or flexibility desired in the final product. The helical coil 22 may be about 3 to about 45 cm in length, preferably about 5 to about 20 cm, has an outer diameter about the same size as the outer diameter of the elongated proximal core section 11, and is made from wire about 0.001 to about 0.003 inch (0.025–0.08 mm) in diameter typically about 0.002 inch (0.05 mm). The shaping ribbon 23 and the flattened distal section 28 of distal core section 12 have generally rectangularly shaped transverse cross-sections which usually have dimensions of about 0.0005 to about 0.006 inch (0.013–0.152 mm), preferably about 0.001 by 0.003 inch (0.025–0.076 mm).

The distal core section 12 is preferably made of a psuedoelastic alloy material consisting essentially of about 30 to about 52% titanium and the balance nickel and up to 10% of one or more other alloying elements. The other alloying elements may be selected from the group consisting of iron, cobalt, vanadium, platinum, palladium and copper. The alloy can contain up to about 10% copper and vanadium and up to 3% of the other alloying elements. The addition of nickel above the equiatomic amounts with titanium and the other identified alloying elements increase the stress levels at which the stress[0a‰o9]nduced austenite-to-martensite transformation occurs and ensures that the temperature at which the martensite phase thermally transforms to the austenite phase is well below human body temperature (37° C.) so that austenite is the only temperature stable phase at body temperature. The excess nickel and additional alloying elements also help to provide an expanded strain range at very high stresses when the stress induced transformation of the austenite phase to the martensite phase occurs.

A presently preferred method for making the pseudoelastic distal core section is to cold work, preferably by drawing, a rod having a composition according to the relative proportions described above and then heat treating the cold worked product while it is under stress to impart a shape memory thereto. Typical initial transverse dimensions of the rod are about 0.045 inch to about 0.25 inch. Before drawing the solid rod, it is preferably annealed at a temperature of about 5000 to about 750° C., typically about 650° C., for about 30 minutes in a protective atmosphere such as argon to relieve essentially all internal stresses. In this manner all of the specimens start the subsequent thermomechanical processing in essentially the same metallurgical condition so that products with consistent final properties are obtained. Such treatment also provides the requisite ductility for effective cold working.

The stressed relieved stock is cold worked by drawing to effect a reduction in the cross sectional area thereof of about 30 to about 70%. The metal is drawn through one or more dies of appropriate inner diameter with a reduction per pass of about 10 to 50%. Other forms of cold working can be employed such as swaging.

Following cold work, the drawn wire product is heat treated at a temperature between about 350° and about 600° C. for about 0.5 to about 60 minutes. Preferably, the drawn wire product is simultaneously subjected to a longitudinal stress between about 5% and about 50%, preferably about 10% to about 30% of the tensile strength of the material (as measured at room temperature) in order to impart a straight "memory" to the metal and to ensure that any residual stresses therein are uniform. This memory imparting heat treatment also fixes the austenite-martensite transformation temperature for the cold worked metal. By developing a straight "memory" and maintaining uniform residual stresses in the pseudoelastic material, there is little or no tendency for a guidewire made of this material to whip when it is torqued within a patient's blood vessel. The term "whip" refers to the sudden rotation of the distal tip of a guidewire when the proximal end of the guidewire is subjected to torque.

An alternate method for imparting a straight memory to the cold worked material includes mechanically straightening the wire and then subjecting the straightened wire to a memory imparting heat treatment at a temperature of about 300° to about 450° C., preferably about 330° to about 400° C. The latter treatment provides substantially improved tensile properties, but it is not very effective on materials which have been cold worked above 55%, particularly above 60%. Materials produced in this manner exhibit stress-induced austenite to martensite phase transformation at very high levels of stress but the stress during the phase transformation is not nearly as constant as the previously discussed method. Conventional mechanical straightening means can be used such as subjecting the material to sufficient longitudinal stress to straighten it.

Because of the extended strain range under stress-induced phase transformation which is characteristic of the pseudoelastic material described herein, a guidewire having a distal portion made at least in substantial part of such material can be readily advanced through tortuous arterial passageways. When the distal end of the guidewire engages the wall of a body lumen such as a blood vessel, it will pseudoelastically deform as the austenite transforms to martensite. Upon the disengagement of the distal end of the guidewire from the vessel wall, the stress is reduced or eliminated from within the pseudoelastic portion of the guidewire and it recovers to its original shape, i.e. the shape "remembered" which is preferably straight. The straight "memory" in conjunction with little or no nonuniform residual longitudinal stresses within the guidewire prevent whipping of the guidewire's distal end when the guidewire is torqued from the proximal end thereof. Moreover, due to the very high level of stress needed to transform the austenite phase to the martensite phase, there is little chance for permanent deformation of the guidewire or the guiding member when it is advanced through a patient's artery.

The present invention provides guidewires which have pseudoelastic characteristics to facilitate the advancing thereof in a body lumen. The guiding members exhibit extensive, recoverable strain resulting from stress induced phase transformation of austenite to martensite at exceptionally high stress levels which greatly minimizes the risk of damage to arteries during the advancement therein.

The connecting element generally may have an outer diameter from about 0.006 inch to about 0.02 inch (0.15–0.51 mm) with wall thickness of about 0.002 to about 0.006 inch (0.05–0.02 mm). A presently preferred hypotubing from which the connecting element is formed has an outer diameter of about 0.014 inch (0.36 mm) and a wall thickness of about 0.005 inch (0. 13 mm). The overall length of the connector may range from about 0.25 to about 3 cm, typically about 0.75 to about 1.5 cm.

The high strength proximal portion of the guidewire generally is significantly stronger, i.e. higher ultimate tensile strength, than the pseudoelastic distal portion. Suitable high strength materials include 304 stainless steel which is a conventional material in guidewire construction. Other high strength materials include nickel- cobalt-molybdenum-chromium alloys such as commercially available MP35N alloy.

To the extent not otherwise described herein, the materials and methods of construction and the dimensions of conventional intravascular guidewires may be employed with the guidewire of the present invention. Moreover, features disclosed with one embodiment may be employed with other described embodiments. While the description of the invention is directed to presently preferred embodiments, various modifications and improvements can be made to the invention without departing therefrom.

What is claimed is:
1. An elongated guidewire comprising:
   an elongated core member having a proximal core section with proximal and distal ends and formed from a first material and a distal core section with proximal and distal ends and formed from a second material different than the first material, wherein at least one of the distal end of the proximal core section and the proximal end of the distal core section has at least one transverse dimension greater than a transverse dimension of a portion of an adjacent section;

a connecting element formed at least in part from a polymeric material and disposed on the distal end of the proximal core section and the proximal end of the distal core section and configured to produce a torque transmitting relationship between the distal end of the proximal core section and the proximal end of the distal core section; wherein a hardenable material contained within the connecting element forms a mechanical interlock with the distal end of the proximal core section.

2. The guidewire of claim 1 wherein the hardenable material contained within the connecting element forms a bond with the proximal end of the distal core section.

3. The guidewire of claim 1 wherein the hardenable material is a polymeric material.

4. An elongated guidewire comprising:

an elongated core member having a proximal core section with proximal and distal ends and formed from a first material and a distal core section with proximal and distal ends and formed from a second material different than the first material;

a connecting element formed at least in part from a polymeric material and disposed on the distal end of the proximal core section and the proximal end of the distal core section and configured to produce a torque transmitting relationship between the distal end of the proximal core section and the proximal end of the distal core section, and the connecting element including a protrusion; wherein a hardenable material contained within the connecting element forms a mechanical interlock with the proximal end of the distal core section and the protrusion of the connecting element.

5. The guidewire of claim 4 wherein the hardenable material contained within the connecting element forms a bond with the distal end of the proximal core section.

6. The guidewire of claim 4 wherein the hardenable material forms a mechanical interlock with the connecting element.

7. The guidewire of claim 4 wherein the second material forming the distal core section is a pseudoelastic material.

8. The guidewire of claim 7 wherein the pseudoelastic material is a nickel-titanium alloy having a thermally stable austenite phase at body temperature.

9. The guidewire of claim 4 wherein the hardenable material is a polymeric material.

10. An elongated guidewire comprising:

an elongated core member having a proximal core section with proximal and distal ends and formed from a first material and a distal core section with proximal and distal ends and formed from a second material different than the first material;

wherein at least one of the distal end of the proximal core section and the proximal end of the distal core section includes a recess;

a connecting element formed at least in part from a polymeric material and disposed on the distal end of the proximal core section and the proximal end of the distal core section and configured to produce a torque transmitting relationship between the distal end of the proximal core section and the proximal end of the distal core section; wherein a hardenable material contained within the connecting element forms with the recess for a mechanical interlock with at least one of the distal end of the proximal core section and the proximal end of the distal core section.

11. The guidewire of claim 10 wherein the connecting element is bonded to at least one of the distal end of the proximal core section and the proximal end of the distal core section.

12. The guidewire of claim 10 wherein the hardenable material contained within the connecting element forms a bond with the other of the at least one of the distal end of the proximal core section and the proximal end of the distal core section.

13. The guidewire of claim 10 wherein the hardenable material is a polymeric material.

14. The guidewire of claim 10, wherein at least one of the distal end of the proximal core section and the proximal end of the distal core section includes an enlarged end.

* * * * *